US011511084B2

(12) United States Patent
Chu

(10) Patent No.: US 11,511,084 B2
(45) Date of Patent: Nov. 29, 2022

(54) INTRODUCER SHEATH

(71) Applicant: Boston Scientific Scimed, Inc., Maple Grove, MA (US)

(72) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 946 days.

(21) Appl. No.: 15/673,111

(22) Filed: Aug. 9, 2017

(65) Prior Publication Data

US 2018/0043138 A1 Feb. 15, 2018

Related U.S. Application Data

(60) Provisional application No. 62/373,630, filed on Aug. 11, 2016.

(51) Int. Cl.
*A61M 25/06* (2006.01)
*A61M 25/00* (2006.01)
*A61B 17/221* (2006.01)
*A61B 17/34* (2006.01)
*A61B 5/283* (2021.01)
*A61N 1/05* (2006.01)
*A61B 90/40* (2016.01)

(52) U.S. Cl.
CPC ......... *A61M 25/0668* (2013.01); *A61B 5/283* (2021.01); *A61B 17/221* (2013.01); *A61B 17/3417* (2013.01); *A61M 25/0074* (2013.01); *A61M 25/0097* (2013.01); *A61B 17/3415* (2013.01); *A61B 17/3431* (2013.01); *A61B 90/40* (2016.02); *A61B 2017/3409* (2013.01); *A61M 2025/0681* (2013.01); *A61N 2001/0578* (2013.01)

(58) Field of Classification Search
CPC .......... A61M 25/0074; A61M 25/0097; A61M 25/01; A61M 25/0668; A61M 2025/0675; A61M 2025/0681; A61M 2025/0687; A61M 39/20; A61M 2039/062–0686
See application file for complete search history.

(56) References Cited

U.S. PATENT DOCUMENTS

| 4,997,424 | A | * | 3/1991 | Little | B26D 3/001 604/161 |
| 5,125,904 | A | * | 6/1992 | Lee | A61M 25/0668 604/161 |
| 5,397,311 | A | * | 3/1995 | Walker | A61M 25/0668 604/160 |
| 6,562,049 | B1 | * | 5/2003 | Norlander | A61M 25/0075 606/108 |
| 6,582,390 | B1 | | 6/2003 | Sanderson | |
| 6,589,212 | B1 | * | 7/2003 | Navis | A61B 17/3421 604/164.01 |

(Continued)

*Primary Examiner* — Emily L Schmidt
*Assistant Examiner* — Antarius S Daniel
(74) *Attorney, Agent, or Firm* — Bookoff McAndrews, PLLC

(57) ABSTRACT

A medical device may include an introducer sheath, having a distal and a proximal end and a lumen extending from the distal end to the proximal end. The introducer sheath may also include a tab formed at the distal end and extending distal to the lumen, and a frangible portion extending between the distal end and the proximal end.

20 Claims, 10 Drawing Sheets

(56) References Cited

U.S. PATENT DOCUMENTS

| | | | | |
|---|---|---|---|---|
| 7,645,296 B2* | 1/2010 | Theron | ............ | A61B 17/12136 |
| | | | | 623/1.11 |
| 8,029,481 B2* | 10/2011 | Reavill | ................ | A61M 25/01 |
| | | | | 604/164.04 |
| 2013/0030414 A1* | 1/2013 | Gardner | ................ | A61M 39/20 |
| | | | | 604/533 |
| 2017/0258489 A1* | 9/2017 | Galili | .................... | A61M 39/02 |

* cited by examiner

INTRODUCER SHEATH

CROSS-REFERENCE TO RELATED APPLICATIONS

This application claims the benefit of priority to U.S. Provisional Application No. 62/373,630, filed Aug. 11, 2016, which is incorporated by reference herein in its entirety.

TECHNICAL FIELD

Various aspects of the present disclosure relate generally to medical devices and related methods. More specifically, the present disclosure relates to medical devices for delivering an elongate device.

BACKGROUND

Medical devices, such as lasers, needles, infusion tubes, sensors, and the like may include an elongate body, and may be arranged for delivery through a working channel of an insertion device (e.g., a ureteroscope, a hysteroscope, a bronchoscope, a cystoscope, and similar devices). The elongate body of such medical devices may be selectively extended and retracted relative to the working channel of the insertion device to deploy or retract the elongate body to perform one or more therapies, treatments, or diagnostic evaluations on a subject. For example, the medical device may include a laser having an elongate body arranged for delivery through a working channel of a ureteroscope. Such elongated medical devices often must be threaded through a seal or valve in order to prevent irrigation or fluid backflow through the port or channel through which the elongated device accesses the insertion device. However, using a seal or valve can be time-consuming because the elongated device must be "inched" through the valve or seal in small increments as the elongated device lacks sufficient stiffness to allow a long pushing of the device through the valve or seal, without the device kinking or being damaged. As such, medical professionals must spend time tediously threading small portions of the elongated device through the seal or valve and into the insertion device. Moreover, if one forgoes using a seal or valve to expedite the insertion of the elongated device into the insertion device, there is the danger of an inadvertent escape of pressurized body fluids or of foreign contaminants entering the patient. Finally, if one uses a thicker covering around the elongated medical device to introduce the elongated medical device into the valve and into the insertion device, such an inducer remains on the elongated device, which makes manipulating the elongated device during the procedure more difficult. These efforts also increase the cost, complexity, and/or risks of the medical procedure involving an insertion device.

The devices and methods of the current disclosure may rectify some of the deficiencies described above or address other aspects of the prior art.

SUMMARY

Examples of the present disclosure relate to, among other things, medical retrieval devices. Each of the aspects disclosed herein may include one or more of the features described in connection with any of the other disclosed aspects.

One aspect of this disclosure is an introducer sheath. The introducer sheath may comprise: a distal and a proximal end; a lumen extending from the distal end to the proximal end; a tab formed at the distal end and extending distal to the lumen; and a frangible portion extending between the distal end and the proximal end.

According to this aspect, the lumen may extend to a proximal end face of the proximal end. The frangible portion may include a slit, a perforation, a reduced thickness, or a gap in the introducer sheath. The frangible portion may also extend in a straight line between the distal end and the proximal end. Furthermore, the frangible portion may be located circumferentially opposite the tab. The introducer sheath may include at least one opening. One of the at least one openings may be in the proximal end. The frangible portion may extend through the at least one opening that is in the proximal end. The frangible portion may extend to a proximal end face of the proximal end. The tab may be an integral portion of the introducer sheath. The tab may also be formed of a separate member from a body of the introducer sheath. A valve may be coupled to the proximal end of the introducer sheath. The valve coupled to the proximal end may at least partially overlap an opening in the proximal end. The opening in the proximal end may be located circumferentially opposite the tab. The introducer sheath may have a length between 70 cm and 80 cm.

Another aspect is a method of introducing a medical device into an insertion device by using an insertion sheath, the medical device including an elongate body and the insertion sheath surrounding a portion of the elongate body, the method comprising: introducing a distal end of the elongate body into a port of the insertion device; pulling a distally extending tab of the introducer sheath to urge the elongate body further into the insertion device; and incrementally separating the introducer sheath from the elongate body during the pulling of the distally extending tab.

According to this aspect, pulling the distally extending tab of the introducer sheath may include causing the introducer sheath to fully separate from the elongate body. The method may further comprise threading, capping, or otherwise attaching a seal or valve to the insertion device after the introducer sheath has been fully separated.

Another aspect is a medical device system. The medical device system may comprise a medical device including an elongate body; an introducer sheath having a distal end and a proximal end, a lumen extending from the distal end to the proximal end, a tab formed at the distal end and extending distal to the lumen, and a frangible portion extending between the distal end and the proximal end, wherein the introducer sheath surrounds the medical device and is coupled to the medical device such that movement of the introducer sheath moves the medical device.

According to this aspect, the medical device system's introducer sheath may include at least one opening, and the frangible portion may pass through and extend beyond the at least one opening toward both the distal end and proximal end. The medical device system may also include a seal or valve positioned around both the introducer sheath and the medical device. The seal or valve may be positioned around at least one opening in the introducer sheath.

Both the foregoing general description and the following detailed description are exemplary and explanatory only and are not restrictive of the features, as claimed. As used herein, the terms "comprises," "comprising," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal."

BRIEF DESCRIPTION OF THE DRAWINGS

The accompanying drawings, which are incorporated in and constitute a part of this specification, illustrate exemplary features of the present disclosure and together with the description, serve to explain the principles of the disclosure.

DETAILED DESCRIPTION

Examples of the present disclosure relate to medical device introducer sheaths for introduction of an elongate body of the medical device into a seal, valve, scope, or port of an insertion device. The introducer sheath may be used to assist in delivery of the elongate body into any appropriate insertion device.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to an operator using the medical device or insertion device or closer to the exterior of the body or patient. In contrast, "distal" refers to a position relatively further away from the operator using the medical device or insertion device, or closer to the interior of the body or patient.

Figure 1:
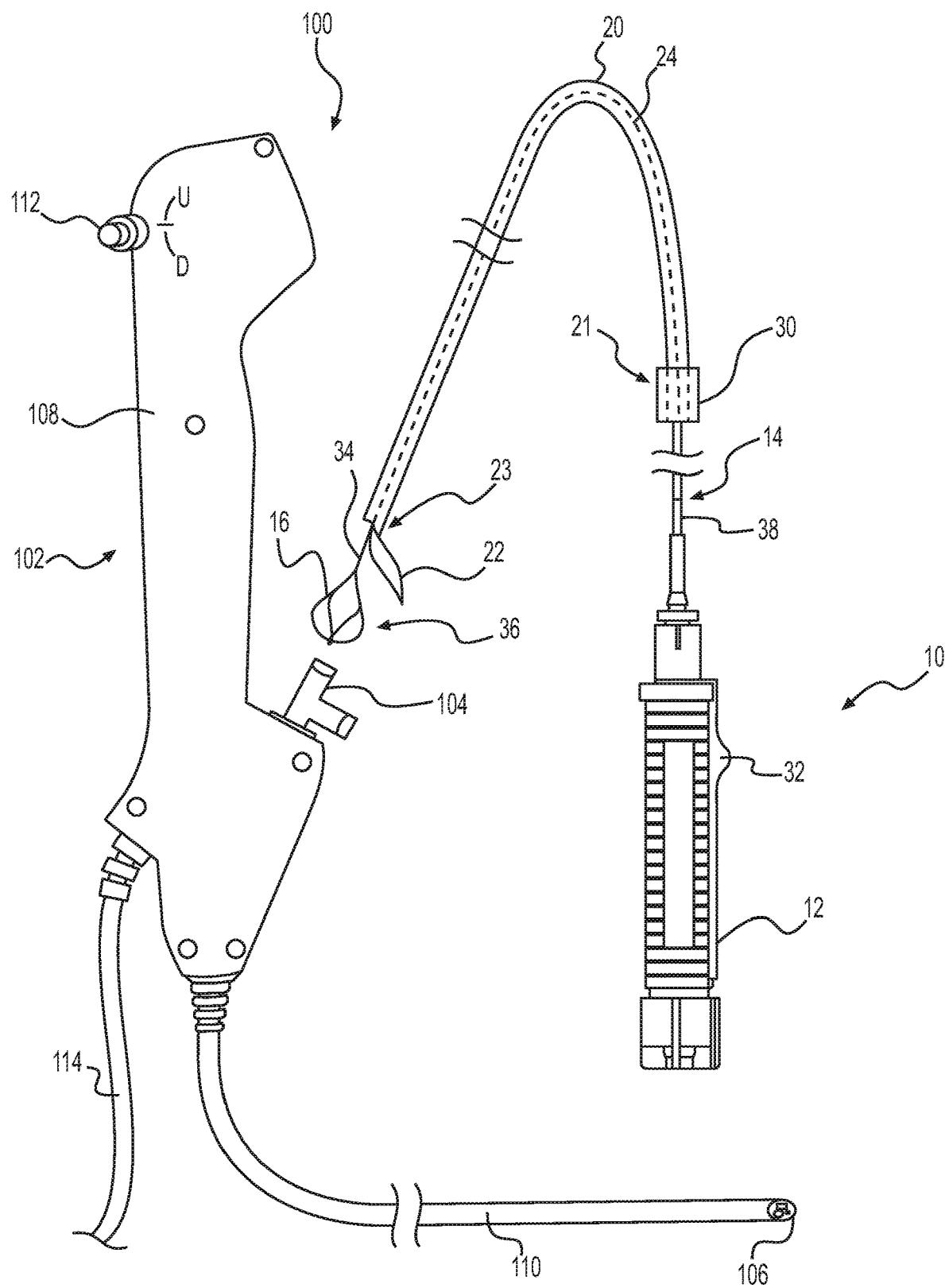
FIG. 1 illustrates an exemplary insertion device, introducer sheath, and medical device to be inserted into the insertion device.

FIG. 1 illustrates a system 100 including an insertion device 102, a medical device 10, and an introducer sheath 20. The insertion device 102 may be a ureteroscope (e.g., LithoVue™ Single-Use Digital Flexible Ureteroscope by Boston Scientific Corp.), an endoscope, a hysteroscope, a bronchoscope, a cystoscope, or any other similar device. The insertion device 102 may include a handle 108, a delivery sheath 110, and an actuator 112 on the handle for steering a distal end 106 of the delivery sheath 110. A port 104, which could be a T-connector as shown, may internally connect one or more lumens extending through the delivery sheath 110 to one or more distal openings in distal end 106 such that various medical devices may be inserted through the delivery sheath 110 of the insertion device 102. Port 104 of the insertion device 102 may include a removable valve 30 (shown detached in FIGS. 1 and 2 and attached to insertion device 102 in FIG. 6). Valve 30 may form a seal by itself or in combination with an element passing through the valve by the valve's seal returning to its normally closed state (e.g., a Urolock™ Adaptor by Boston Scientific Corp.) or by the compression of a grommet by a user's hand (e.g., a Touhy Borst valve). The insertion device 102 may include an integral camera at distal end 106 that is connected to processing software and a display via a communication and power conduit 114.

Medical device 10 will be described as a retrieval basket device; however, it is understood that medical device 10 may be any type of medical device used in conjunction with insertion device 102 to deliver medical therapy to a target site inside a patient. For example, the medical device may alternatively be a laser fiber, an irrigation and/or aspiration tube, a snare, forceps, and/or a needle.

Figure 2:
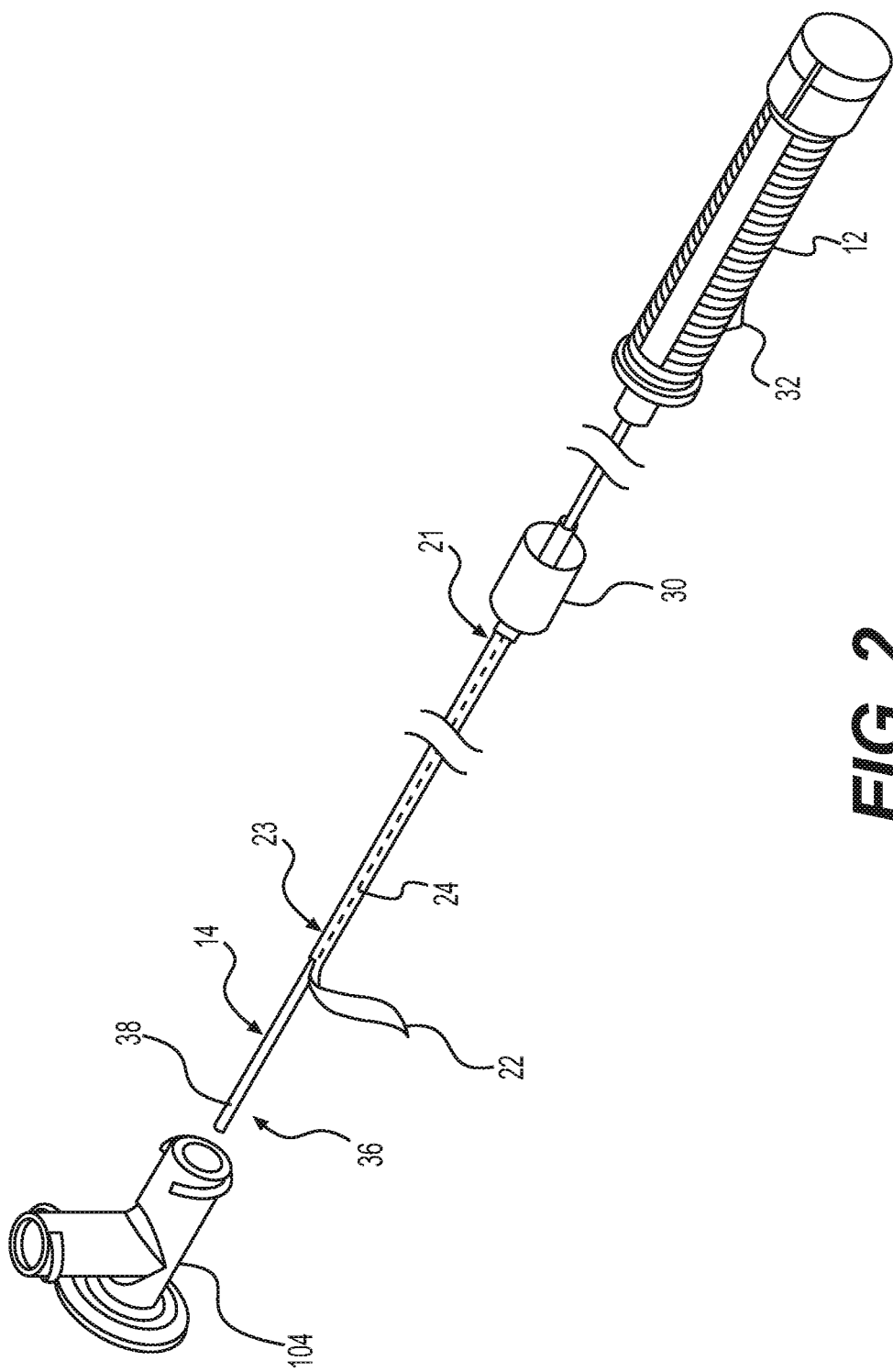
FIG. 2 illustrates a partial view of the exemplary insertion device with the introducer sheath and medical device of FIG. 1.

As shown in FIGS. 1 and 2, the medical device 10 may include a handle 12 and an elongate body 14. Handle 12 may include an actuator 32 for controlling the opening (FIG. 1) and closing (FIG. 2) of a retrieval basket 16 of medical device 10. Elongate body 14 may have a length of between 70 cm and 220 cm and may extend from the handle 12 to a distal end 36 of the medical device 10. Elongate body 14 may include a shaft 34 connecting the handle 12 to retrieval basket 16. Elongate body 14 may also include a sheath 38 connected to actuator 32 to sheath and unsheath retrieval basket 16 corresponding to the open and closed basket configurations shown in FIGS. 1 and 2, respectively.

Figure 3:
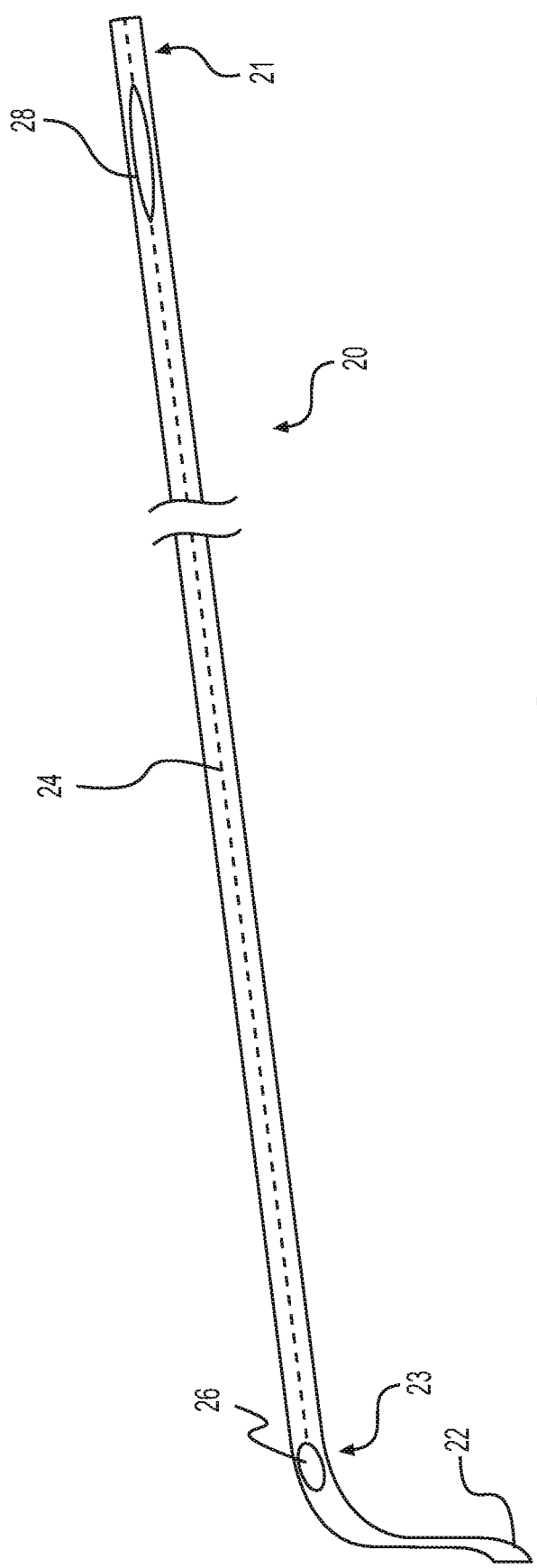
FIG. 3 illustrates an exemplary view of the introducer sheath shown in FIG. 1.

As shown in FIGS. 1-3, introducer sheath 20 may be positioned about elongate body 14 and include a proximal end 21 and a distal end 23, and may include a lumen extending from the proximal end 21 to the distal end 23. The lumen may extend to a proximal end face of the proximal end. In particular, introducer sheath 20 may include a first opening 26 in the distal end 23. A tab 22 may be formed distal to the first opening 26 and extend distal to the lumen. Tab 22 may be a flattened integral portion of introducer sheath 20, a curved portion, or may take any shape that allows a user to hold or pinch the distal end 23 of the introducer sheath 20 extending from the first opening 26. Tab 22 may also be formed of a separate member from a body of the introducer sheath. A second opening 28 may also be included in the proximal end 21 of introducer sheath 20.

Introducer sheath 20 may include a frangible portion 24 along the length of the introducer sheath 20, extending between the distal end 23 and the proximal end face of the proximal end 21. Frangible portion 24 may be formed by cutting a slit along the length of the introducer sheath 20. Frangible portion 24 may also be formed by a perforation or reduced thickness portion of the introducer sheath 20, or by a longitudinally extending gap or discontinuity in the introducer sheath 20. Frangible portion 24 may be formed from the first opening 26 at the distal end 23 to the proximal end face of proximal end 21, and frangible portion 24 may run in a straight line from the first opening 26 at the distal end 23 to the proximal end face of proximal end 21. Frangible portion 24 may be the same length as the introducer sheath 20, or a shorter length. Frangible portion 24 may be located circumferentially opposite tab 22 and aligned with a longitudinal axis of second opening 28 so that the frangible portion 24 ends at a distal end of second opening 28 and starts again at a proximal end of second opening 28. It is understood, however, that frangible portion 24 may be located at any circumferential position along introducer sheath 20.

Introducer sheath 20 may be circular (FIG. 3), hexagonal, oval, or any cross-sectional shape. Moreover, introducer sheath 20 may have a C-shaped cross-section such that the introducer sheath 20 may be snapped or wrapped around the elongate body 14. In such a C-shaped configuration, frangible portion 24 is formed by the gap of the C-shape.

Introducer sheath 20 may be formed by a tubular extrusion. Introducer sheath 20 may also be formed by sizing a tubular extrusion to the outer diameter of elongate body 14. Frangible portion 24 may then be formed in the introducer sheath 20. For example, frangible portion 24 may be formed by cutting a slit with a scalpel inserted into the outer diameter of introducer sheath 20. The introducer sheath 20 may be dragged against the scalpel lengthwise to form frangible portion 24. Alternatively, frangible portion 24 may be formed by cutting a slit in introducer sheath 20 while introducer sheath 20 is being formed or extruded. Moreover, frangible portion 24 may be formed as the gap in a C-shaped tubular extrusion forming introducer sheath 20. Such a C-shaped introducer sheath 20 may be reheated to form a circular cross-sectional shape, where the edges of the C-shaped configuration overlap. A C-shaped introducer sheath may also be formed by heating a flat strip of material through a smaller die to create a C-shaped configuration or a circular cross-sectional shape, where the edges of the C-shaped configuration overlap.

Introducer sheath 20 may be formed of elastomeric. Introducer sheath 20 may also be formed of silicone, thermoplastic elastomer, ethylene-propylene, fluorocarbon, or other similar materials.

The introducer sheath 20 may be matched to a specific elongate body 14 of a specific medical device 10 such that the introducer sheath's inner diameter and length correspond to the specific elongate body 14 and specific medical device 10. In another example, the introducer sheath 20 may have an inner diameter slightly smaller than the outer diameter of the elongate body 14 of the medical device 10 such that, when coupled, the introducer sheath 20 snugly encircles the elongate body 14. In a further example, the introducer sheath 20 may have an inner diameter equal to or slightly larger than the outer diameter of the elongate body 14 of the medical device 10 such that, when coupled, the introducer sheath 20 is free to slide along the elongate body 14 when the introducer sheath 20 and the elongate body 14 are in a straight condition, but are friction coupled when either the introducer sheath 20 or elongate body 14, or both elements, are curved, bent, or otherwise not straight.

The introducer sheath 20 and elongate body 14 may form alternative or additional frictional engagements, couplings, or associations. For example, as shown in FIGS. 1 and 2, valve 30 may be removed from port 104 and positioned about and coupled to the proximal end 21 of the introducer sheath 20. Valve 30 may provide enough compression force on introducer sheath 20 to couple introducer sheath 20 with elongate body 14. For example, valve 30 may be positioned about the second opening 28 and compress this more flexible portion of introducer sheath 20 to frictionally couple the introducer sheath 20 and the elongated device 14.

Figure 4:
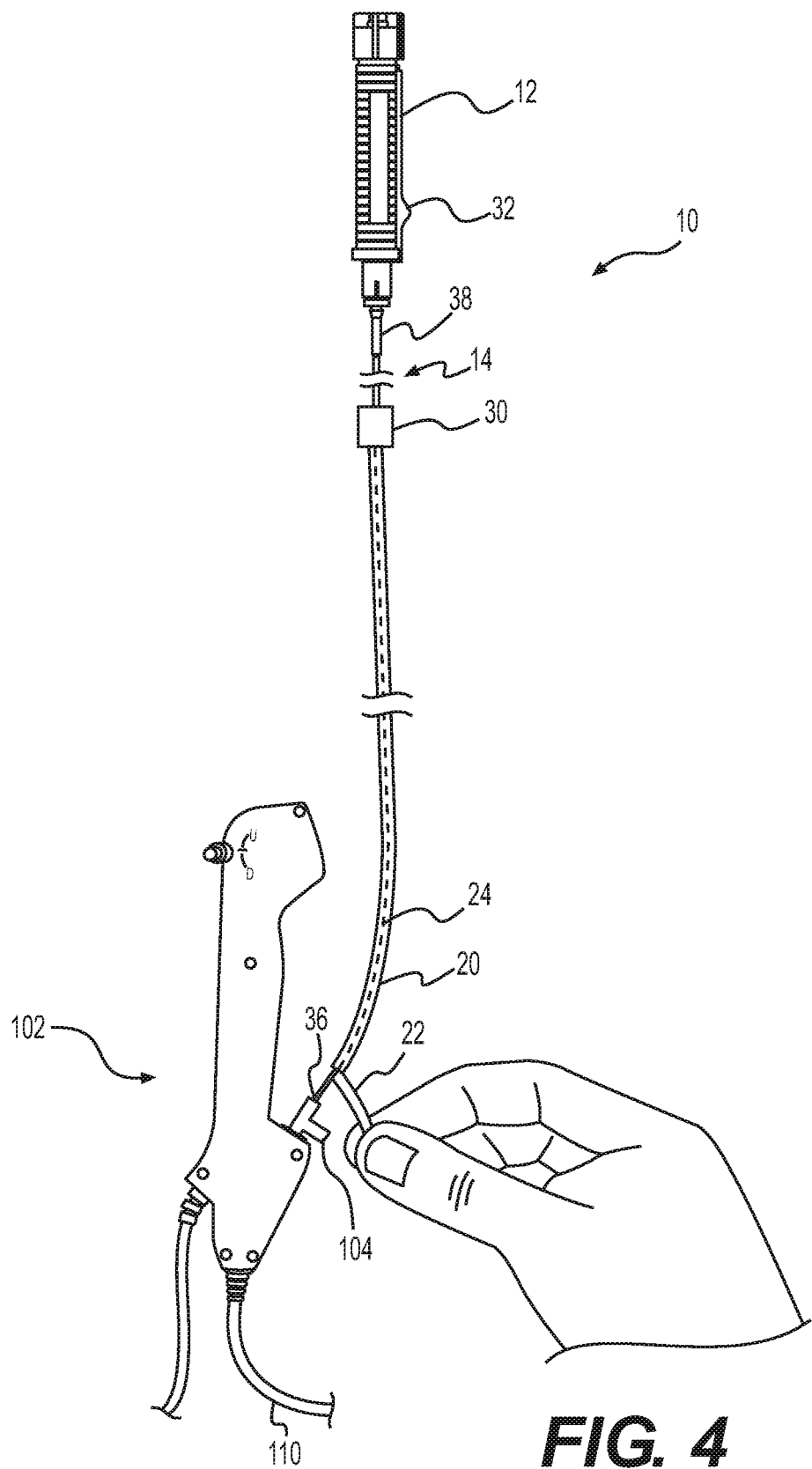
FIGS. 4-6 illustrate the operation of the introducer sheath in the system of FIGS. 1-3.
Figure 5:
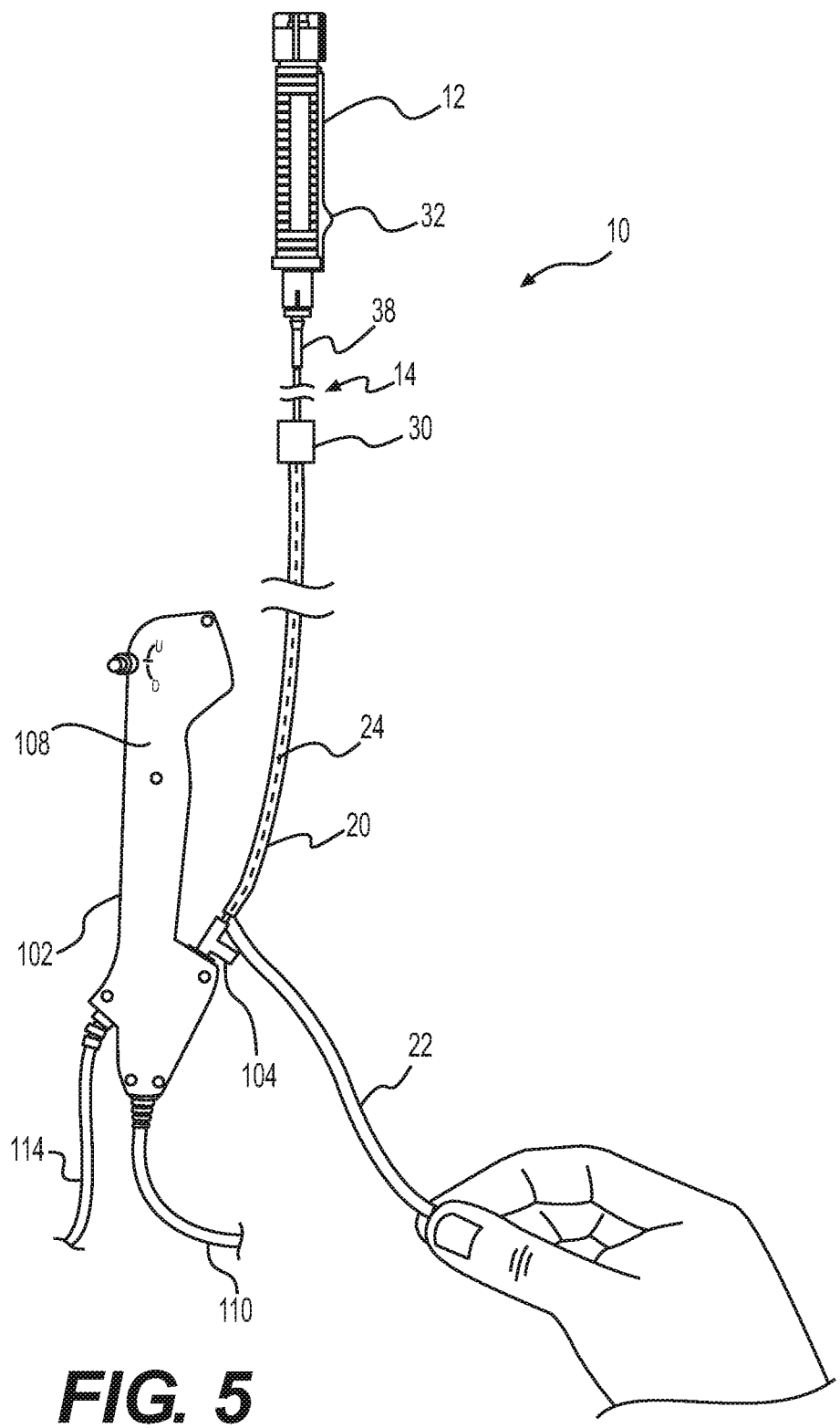
Figure 6:
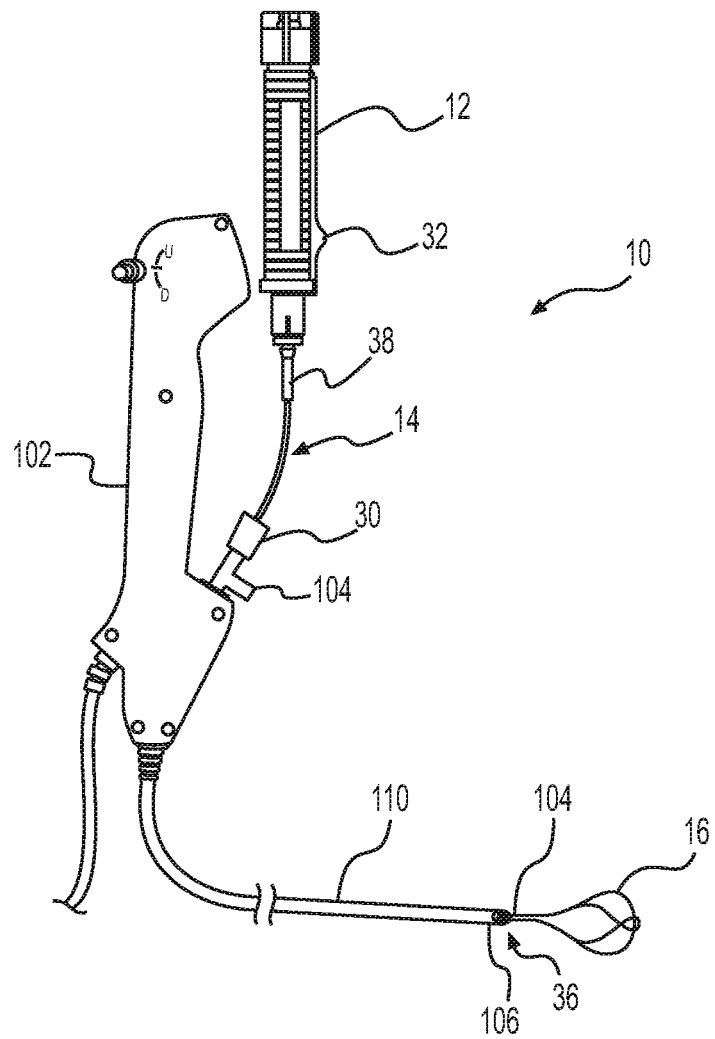

Next, FIGS. 4-6 illustrate the rapid introduction of the medical device 10 into insertion device 102 through the use of introducer sheath 20. As shown in FIG. 4, the distal end 36 of the elongate body 14, which extends distally beyond the introducer sheath 20, is introduced into the insertion device 102 via a port 104. The tab 22 of introducer sheath 20 may be angled away from the port 104 such that the tab 22 can be held by a user. As shown in FIG. 5, the tab 22 can be pulled away from and deflected by port 104 to separate the introducer sheath 20 from the elongate body 14 about the frangible portion 24. Due to the coupling between the introducer sheath 20 and the elongate body 14, as the user pulls the tab 22 toward a distal end of handle 108 to further separate the introducer sheath 20 from the elongate body 14, the elongate body 14 is moved distally therewith and thus is rapidly introduced into the insertion device 102. Continued pulling of the tab 22 distally causes introducer sheath 20 to separate from the elongate body 14 until the valve 30 reaches port 104 of the insertion device 102. Further distal pulling on the tab 22 fully separates the introducer sheath 20 from both the elongate body 14 and valve 30, resulting in the valve 30 being located adjacent port 104 of the insertion device 102 (FIG. 6). Lastly, the valve 30 may be threaded, capped, or otherwise attached to the port 104 to complete the introduction of the elongate body 14 into the insertion device 102.

It should be noted that the relationship of the length of the elongate body 14 and introducer sheath 20 determines the position of the distal end 36 of the elongate body 14, and thus the retrieval basket 16, relative to the distal end 106 of the insertion device 102 after completing the introduction via introducer sheath 20. Different types of scopes vary in working length from approximately 70 cm to approximately 220 cm. In some examples, the introducer sheath 20 has a length such that, when the proximal end 21 of introducer sheath 20 is located adjacent port 104, the distal end 36 of the elongate body 14 and the retrieval basket 16 are positioned flush with the distal end 106, just proximal to the distal end 106, or just distal to the distal end 106 (FIG. 6). For example, introducer sheath 20 may have a length between 70 cm and 80 cm when used in conjunction with a 75 cm scope. As noted above, the introducer sheath 20 may range in length depending on the type of medical device 10, elongate body 14, retrieval basket 16, insertion device 102, medical procedure, and other factors.

Another aspect of the present disclosure is described with reference to FIGS. 7 and 8. In this example, an introducer sheath 70 is used to protect fragile or sensitive components in the elongate body 14 and the retrieval basket 16 as they move in a direction D to pass through a normally closed seal or valve 40 attached to port 104 of the insertion device 102 (FIG. 8). Here, the normally closed seal or valve 40 may be part of a valve system that includes valve 30, as previously discussed with respect to FIGS. 1-6. Normally closed seal or valve 40 may be used in conjunction with valve 30 to form an adjustable seal.

Figure 7:
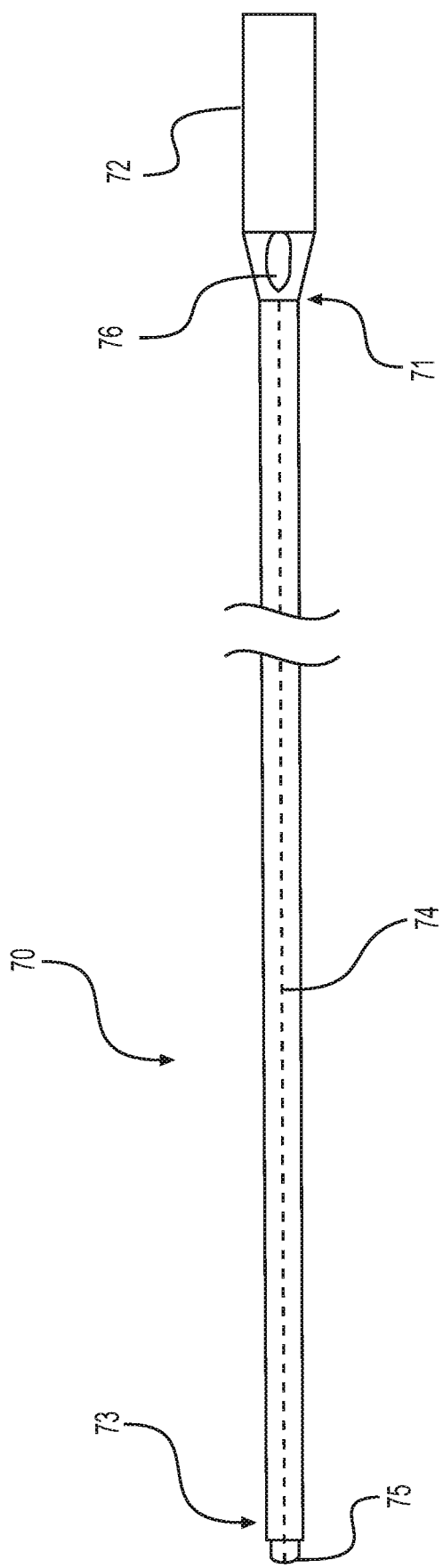
FIG. 7 illustrates a further exemplary introducer sheath.
Figure 8:
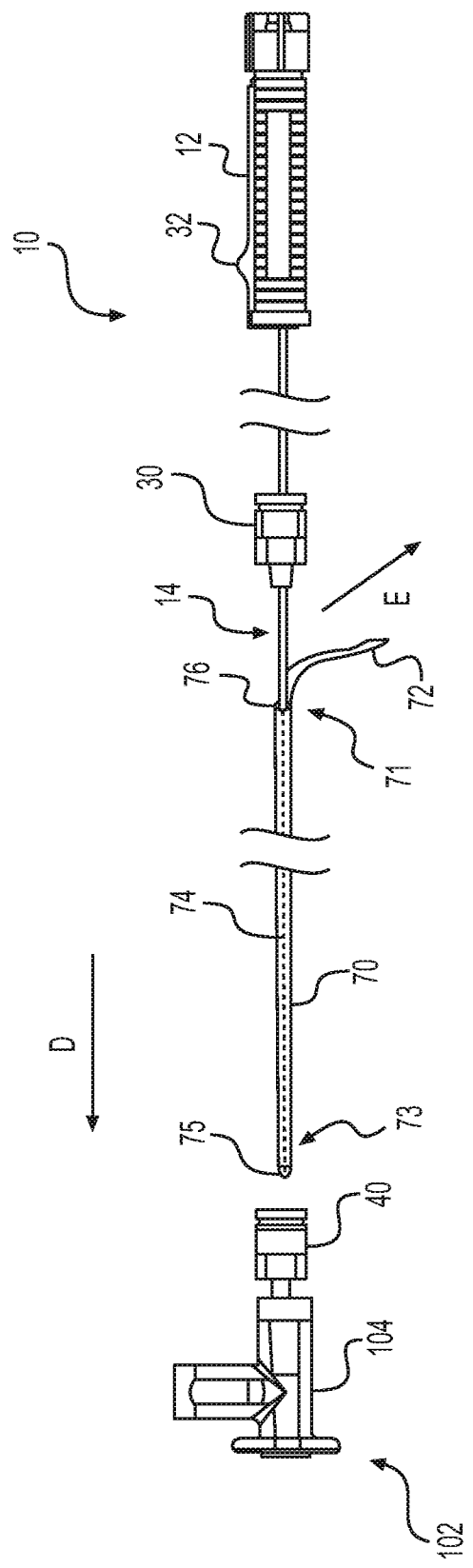
FIG. 8 illustrates an exploded view of the insertion device and a further medical device with the introducer sheath shown in FIG. 7.

FIG. 7 illustrates the introducer sheath 70 with tapered tip 75 at the distal end 73 and a first opening 76 at the proximal end 71. Although tapered tip 75 is narrower than the remaining portion of introducer sheath 70, tapered tip 75 is open such that elongate body 14 may pass fully through and out of either end of introducer sheath 70. A frangible portion 74 runs the length of the introducer sheath 70 from the tapered tip 75 to the first opening 76, and a tab 72 extends from the first opening 76 on the proximal end of the introducer sheath 70 and circumferentially opposite to the frangible portion 74. This introducer sheath 70 may range in length between approximately 1 cm and approximately 10 cm depending on the type of medical device 10, elongate body 14, retrieval basket 16, insertion device 102, medical procedure, and other factors. Moreover, the inner diameter of the introducer sheath 70 may be slightly larger than the outer diameter of the elongate body 14 so that the elongate body 14 may slide axially through the introducer sheath 70 and the introducer sheath 70 may slide axially over the elongate body 14, as shown in FIG. 8.

To insert the fragile or sensitive components of the elongate body 14, including the retrieval basket 16 through the normally closed seal or valve 40, the introducer sheath 70 surrounds the elongate body 14, including the distal end 36 which is not shown in FIG. 8 as it is surrounded by the introducer sheath 70. The tapered tip 75, which includes an axial opening large enough for elongate body 14 to pass through, is inserted into the normally closed seal or valve 40 to prop open the valve. The elongate body 14 may then axially slide in the distal direction through the inner diameter of the introducer sheath 70 and through the tapered tip 75 in direction D, such that distal end 36 of elongate body 14 may emerge and slide distal to the tapered tip 75 and be selectively positioned distal to the normally closed seal or valve 40.

After the distal end 36 of elongate body 14 has been positioned past the normally closed seal or valve 40, the tapered tip 75 of the introducer sheath 70 may be retracted proximally to close the normally closed seal or valve 40 around the elongate body 14. The user may elect to leave the introducer sheath 70 on the elongate body 14 proximal to the normally closed seal or valve 40, allowing the user to prop open the normally closed seal or valve 40 again with tapered tip 75 to adjust the position of the normally closed seal or valve 40 relative to elongate body 14. The user may also elect to remove the introducer sheath 70 by pulling the tab 72 in a direction E away from the elongate body 14, such that the frangible portion 74 splits and separates the introducer sheath 70 from the elongate body 14. Removing the introducer sheath 70 from the elongate body 14 may allow for a longer working length of the elongate body 14 and avoid interference or obstruction from the introducer sheath 70 during manipulation of the elongate body 14 during the medical procedure. Valve 30 may also then be threaded, capped, or otherwise attached to normally closed seal or valve 40.

Alternatively, the tapered tip 75 may be inserted into the normally closed seal or valve 40, and the distal end 36 of elongate body 14 together with the surrounding introducer sheath 70 may pass in direction D through the normally closed seal or valve 40, allowing for the introducer sheath 70 to shield the fragile or sensitive components in the elongate body 14.

Once the distal end 36 of elongate body 14 has been positioned distally to the normally closed seal or valve 40, the introducer sheath 70 and the tapered tip 75 may be retracted proximally such that the elongate body 14 emerges from the opening in tapered tip 75 and such that normally closed seal or valve 40 closes around the elongate body 14. The user may elect to leave the introducer sheath 70 on the elongate body 14 proximal to the normally closed seal or valve 40, allowing the user to prop open the normally closed seal or valve 40 again with tapered tip 75 and introducer sheath 70 to adjust the position of the normally closed seal or valve 40 relative to elongate body 14. The user may also elect to remove the introducer sheath 70 by pulling the tab 72 in a direction E away from the elongate body 14, such that the frangible portion 74 splits and separates the introducer sheath 70 from the elongate body 14, which may allow for a longer working length of the elongate body 14 and avoid interference or obstruction from the introducer sheath 70 during manipulation of the elongate body 14 during the medical procedure. Valve 30 may also then be threaded, capped, or otherwise attached to normally closed seal or valve 40. In this example where introducer sheath 70 passes through normally closed seal or valve 40 together with elongate body 14, introducer sheath 70 may be longer than the 1 cm to 10 cm length previously discussed with respect to this aspect of the disclosure.

Another aspect of the present disclosure is described with reference to FIGS. 9 and 10. In this example, an introducer sheath 90 is used to protect fragile or sensitive components in the elongate body 14 and the retrieval basket 16 as they move in a direction F and pass through a normally closed seal or valve 50 that is not coupled to an insertion device. Using introducer sheath 90 allows normally closed seal or valve 50, which is manufactured separately from medical device 10, to be selectively positioned along elongate body 14 of medical device 10 more quickly while protecting the fragile or sensitive components. Moreover, as a result, insertion of elongate body 14 into a port 104 of an insertion device 102 similar to that in FIG. 1 or any scope or medical device channel is made easier because positioning the normally closed seal or valve 50 proximally along elongate body 14 reduces resistance and thus provides for a better insertion.

Figure 9:
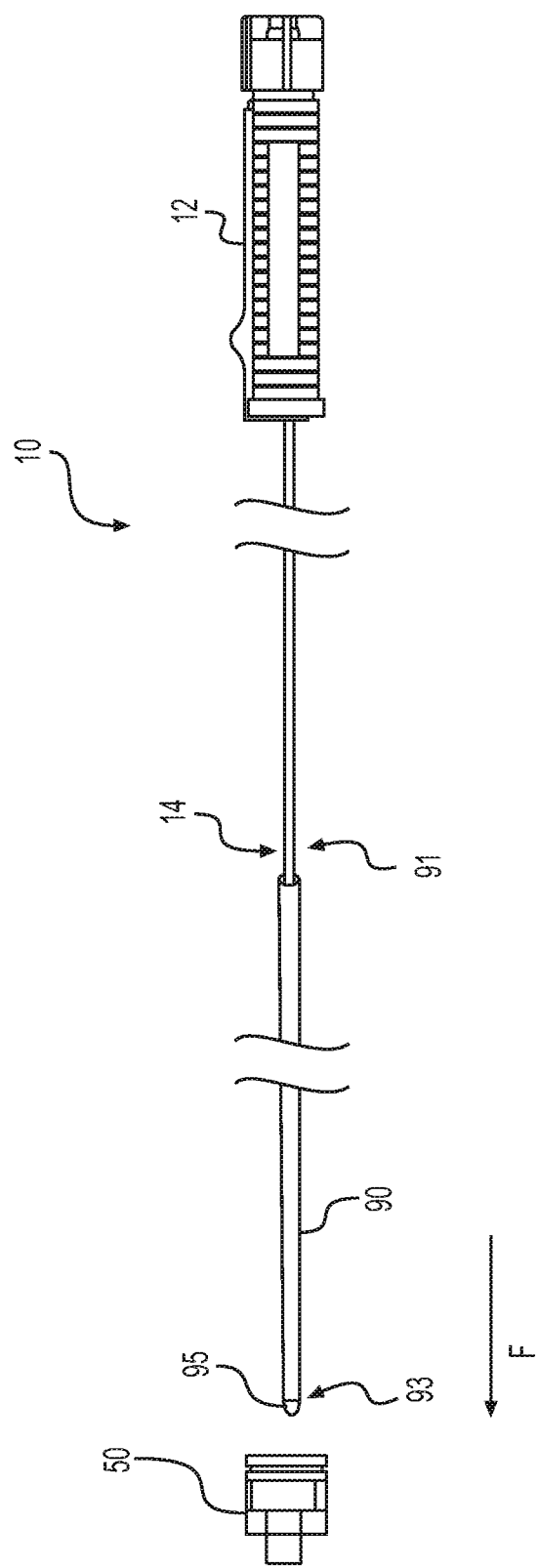
FIG. 9 illustrates a further exemplary introducer sheath, a medical device, and a valve.
Figure 10:
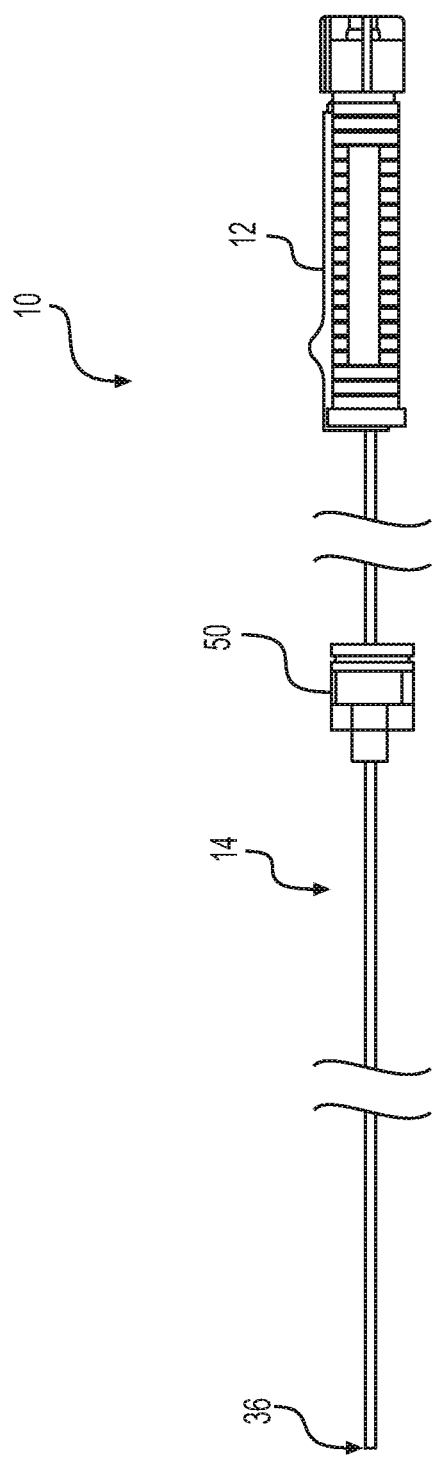
FIG. 10 illustrates the medical device and valve of FIG. 9.

Here, FIG. 9 illustrates the introducer sheath 90 with a tapered tip 95 at a distal end 93. Although tapered tip 95 is narrower than the remaining portion of introducer sheath 90, tapered tip 95 is open such that distal end 36 of elongate body 14 may pass fully through and out of either end of introducer sheath 90. Again, this introducer sheath 90 may range in length between approximately 1 cm and approximately 10 cm depending on the type of medical device 10, elongate body 14, retrieval basket 16, medical procedure, and other factors. In this example, the inner diameter of the introducer sheath 90 may be slightly larger than the outer diameter of the elongate body 14 so that the elongate body 14 may slide axially through the introducer sheath 90 and the introducer sheath 90 may slide axially over the elongate body 14, as shown in FIGS. 9 and 10.

To insert the fragile or sensitive components of the elongate body 14 through the normally closed seal or valve 50 in direction F, the introducer sheath 90 surrounds the elongate body 14, including the distal end 36 which is not shown in FIG. 9 as it is surrounded by the introducer sheath 90. The tapered tip 95 is inserted into the normally closed seal or valve 50 to prop open the valve. The elongate body 14 of the medical device 10 may then follow through the normally closed seal or valve 50 by sliding axially through the inner diameter of the introducer sheath 90 in the distal direction. After the distal end 36 of the elongate body 14 has been selectively positioned past the normally closed seal or valve 50, the tapered tip 95 of the introducer sheath 90 may be retracted proximally to close the normally closed seal or valve 50 around the elongate body 14, allowing the user to prop open the normally closed seal or valve 50 again with tapered tip 95 to adjust the position of the normally closed seal or valve 50 relative to elongate body 14.

Alternatively, once the tapered tip 95 has been inserted to prop open the normally closed seal or valve 50, both the introducer sheath 90 and the elongate body 14 may be inserted in direction F through the normally closed seal or valve 50 with the introducer sheath 90 protecting the fragile or sensitive components of the elongate body 14 and the retrieval basket 16. After the distal end 36 of the elongate body 14 has been selectively positioned past the normally closed seal or valve 50, that is, when the normally closed seal or valve 50 is selectively positioned along the elongate body 14, the user may retract the introducer sheath 90 and its tapered tip 95 to close the normally closed seal or valve 50 and may elect to leave the introducer sheath on the elongate body 14 on the proximal side of the normally closed seal or valve 50, allowing the user to prop open the normally closed seal or valve 50 again with tapered tip 95 and introducer sheath 90 to adjust the position of the normally closed seal or valve 50 relative to elongate body 14.

The user may also elect to remove the introducer sheath 90 after the distal end 36 of the elongate body 14 has been selectively positioned past the normally closed seal or valve 50 by pulling the introducer sheath 90 distally fully past the normally closed seal or valve 50 in direction F such that the normally closed seal or valve 50 closes around the elongate body 14. Then, the user may continue to slide the introducer sheath 90 in direction F off the distal end 36 of the elongate body 14, removing the introducer sheath 90. As a result, the normally closed seal or valve 50 may be positioned more quickly on the elongate body 14 at the desired position, as shown in FIG. 10, and the introducer sheath 90 will not interfere or obstruct the manipulation of the elongate body 14 during the medical procedure. Moreover, insertion of elongate body 14 into a port 104 of an insertion device 102 similar to that in FIG. 1 or any scope or medical device channel is made easier because positioning the normally closed seal or valve 50 proximally along elongate body 14 reduces resistance and thus provides for a better insertion. Normally closed seal or valve 50 could then be threaded, capped, or otherwise attached to the port 104 of the insertion device 102. In this example where introducer sheath 90 passes through normally closed seal or valve 50 together with elongate body 14, introducer sheath 90 may be longer than the 1 cm to 10 cm length previously discussed with respect to this aspect of the disclosure.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

I claim:

1. An introducer sheath, comprising:
   a distal and a proximal end;
   a lumen extending from the distal end to the proximal end;
   a tab formed at the distal end, wherein the tab extends distal to the lumen and at an angle away from the lumen; and
   a frangible portion extending between the distal end and the proximal end,
   wherein the introducer sheath is configured to assist in the delivery of a medical device into an insertion device, and wherein the introducer sheath is configured to surround a medical device and to be coupled to the medical device such that movement of the tab of the introducer sheath distally moves the medical device distally into the insertion device such that a port of the insertion device separates a portion of the introducer sheath from the medical device.

2. The introducer sheath according to claim 1, wherein the lumen extends to a proximal end face of the proximal end.

3. The introducer sheath according to claim 1, wherein the frangible portion includes a slit, a perforation, a reduced thickness, or a gap in the introducer sheath.

4. The introducer sheath according to claim 1, wherein the frangible portion extends in a straight line between the distal end and the proximal end.

5. The introducer sheath according to claim 1, wherein the frangible portion is located circumferentially opposite the tab.

6. The introducer sheath according to claim 1, further including at least one opening.

7. The introducer sheath according to claim 6, wherein one of the at least one openings is in the proximal end.

8. The introducer sheath according to claim 7, wherein the frangible portion extends through the at least one opening that is in the proximal end.

9. The introducer sheath according to claim 8, wherein the frangible portion extends to a proximal end face of the proximal end.

10. The introducer sheath according to claim 1, wherein the tab is an integral portion of the introducer sheath.

11. The introducer sheath according to claim 1, wherein the tab is formed of a separate member from a body of the introducer sheath.

12. The introducer sheath according to claim 1, wherein a valve is coupled to the proximal end.

13. The introducer sheath according to claim 1, wherein a length of the introducer sheath is between 70 cm and 80 cm.

14. A method of introducing a medical device into an insertion device by using an introducer sheath, the medical device including an elongate body and the introducer sheath surrounding a portion of the elongate body, the method comprising:
   introducing a distal end of the elongate body into a port of the insertion device;
   pulling a distally extending tab of the introducer sheath to urge the elongate body distally further into the insertion device, wherein the introducer sheath includes a lumen, wherein the distally extending tab extends at an angle away from the lumen, and wherein pulling the distally extending tab includes pulling the distally extending tab away from the insertion device such that the tab and a portion of the introducer sheath is separated from the elongate body by a port of the insertion device; and
   incrementally separating the introducer sheath from the elongate body during the pulling of the distally extending tab.

15. The method of claim 14, further comprising:
   pulling the distally extending tab of the introducer sheath such that the introducer sheath fully separates from the elongate body.

16. The method of claim 15, further comprising threading, capping, or otherwise attaching a seal or valve to the insertion device after the introducer sheath has been fully separated.

17. A medical device system, comprising:
   a medical device including an elongate body;
   an insertion device including a port and a delivery sheath, wherein the delivery sheath is configured to be delivered to a target site in a patient; and
   an introducer sheath having a distal end and a proximal end, a lumen extending from the distal end to the proximal end, a tab formed at the distal end and extending distal to and at an angle away from the lumen, and a frangible portion extending between the distal end and the proximal end,
   wherein the introducer sheath surrounds the medical device and is coupled to the medical device such that movement of the tab of the introducer sheath moves the medical device distally into the insertion device, and wherein the tab is configured to be pulled away from and deflected by the port to separate the introducer sheath from the elongate body.

18. The medical device system of claim 17, wherein the introducer sheath includes at least one opening and where the frangible portion passes through and extends beyond the at least one opening toward both the distal end and proximal end.

19. The medical device system of claim 17, further comprising a seal or valve positioned around both the introducer sheath and the medical device.

20. The medical device system of claim 19, wherein the seal or valve is positioned around at least one opening in the introducer sheath.

\* \* \* \* \*